(12) United States Patent
Zhang et al.

(10) Patent No.: US 10,114,241 B2
(45) Date of Patent: Oct. 30, 2018

(54) METHOD AND DEVICE FOR MEASURING MURA LEVEL OF LIQUID CRYSTAL DISPLAY DEVICE

(71) Applicants: BOE TECHNOLOGY GROUP CO., LTD., Beijing (CN); HEFEI BOE OPTOELECTRONICS TECHNOLOGY CO., LTD., Anhui (CN)

(72) Inventors: Yisan Zhang, Beijing (CN); Chun Wang, Beijing (CN); Junsheng Chen, Beijing (CN); Yuanhui Guo, Beijing (CN); Yan Wang, Beijing (CN)

(73) Assignees: BOE TECHNOLOGY GROUP CO., LTD., Beijing (CN); HEFEI BOE OPTOELECTRONICS TECHNOLOGY CO., LTD., Anhui (CN)

(*) Notice: Subject to any disclaimer, the term of this patent is extended or adjusted under 35 U.S.C. 154(b) by 0 days.

(21) Appl. No.: 15/234,001

(22) Filed: Aug. 11, 2016

(65) Prior Publication Data
US 2017/0261776 A1    Sep. 14, 2017

(30) Foreign Application Priority Data
Mar. 11, 2016  (CN) .......................... 2016 1 0140930

(51) Int. Cl.
| G01N 21/00 | (2006.01) |
| G02F 1/13 | (2006.01) |
| G01J 1/04 | (2006.01) |
| G01J 1/16 | (2006.01) |

(52) U.S. Cl.
CPC .......... *G02F 1/1309* (2013.01); *G01J 1/0403* (2013.01); *G01J 1/16* (2013.01)

(58) Field of Classification Search
CPC .......... G06T 7/0004; G01N 2021/9513; G01N 21/958; G09G 3/006
USPC ......... 356/237.1–237.5, 239.1–239.3, 239.7, 356/239.8; 382/141, 149, 203; 348/126; 345/428, 690, 904, 87
See application file for complete search history.

(56) References Cited

U.S. PATENT DOCUMENTS

| 5,917,935 | A  | * | 6/1999  | Hawthorne ........... | G02F 1/1303 348/126 |
| 7,443,498 | B2 | * | 10/2008 | Yoshida .................... | G03F 1/84 356/237.5 |
| 7,932,917 | B2 | * | 4/2011  | Han ........................ | G09G 3/006 324/760.01 |
| 8,160,351 | B2 | * | 4/2012  | Sandstrom ........... | G01N 21/956 356/237.4 |
| 8,743,215 | B1 | * | 6/2014  | Lee ......................... | G09G 3/006 348/180 |

(Continued)

*Primary Examiner* — Hoa Pham
(74) *Attorney, Agent, or Firm* — Brooks Kushman P.C.

(57) ABSTRACT

The present disclosure provides a method and a device for measuring mura levels of liquid crystal display devices. The method includes steps of: acquiring correspondence between standard brightness data differences and standard mura levels; acquiring a measurement brightness data difference of a test image displayed by a to-be-tested liquid crystal display device before and after the measurement; and acquiring a mura level corresponding to the measurement brightness data difference in accordance with the correspondence.

6 Claims, 5 Drawing Sheets

(56) References Cited

U.S. PATENT DOCUMENTS

| | | | | |
|---|---|---|---|---|
| 8,780,097 B2* | 7/2014 | Xu | ............................ | G09G 3/006 345/204 |
| 2005/0007364 A1* | 1/2005 | Oyama | .................. | G02F 1/1309 345/428 |
| 2006/0158642 A1* | 7/2006 | Tanaka | .................. | G01N 21/956 356/237.5 |
| 2015/0346557 A1* | 12/2015 | Lee | .................... | G02F 1/133723 349/128 |
| 2016/0140917 A1* | 5/2016 | Hyung | .................. | G09G 3/3648 345/694 |
| 2017/0193928 A1* | 7/2017 | Deng | .................... | G09G 3/3426 |

* cited by examiner

METHOD AND DEVICE FOR MEASURING MURA LEVEL OF LIQUID CRYSTAL DISPLAY DEVICE

CROSS-REFERENCE TO RELATED APPLICATIONS

This application claims priority to Chinese application No. 201610140930.6, filed Mar. 11, 2016, which is hereby incorporated by reference in its entirety.

TECHNICAL FIELD

The present disclosure relates to the field of liquid crystal display technology, in particular to a method and a device for measuring mura levels of liquid crystal display devices.

BACKGROUND

As a main structure of a liquid crystal display device, a display panel includes an array substrate and a color filter substrate arranged opposite to each other to form a cell, and liquid crystals arranged between the array substrate and the color filter substrate. During the cell formation, alignment films are applied onto inner surfaces of the array substrate and the color filter substrate, so as to enable liquid crystal molecules to be arranged in a certain direction through a corresponding alignment process. Then, the cell is formed through a vacuum cell-forming process.

Usually, a cell thickness of the display panel is controlled via a spacer arranged on the color filter substrate, and cell thickness uniformity is a very important index for the quality of the liquid crystal display device. In the case that an external force is applied to a surface of the display panel, the display panel may be deformed, and in the case of the sufficient large external force, the color filter substrate and the array substrate may be displaced relative to each other. Due to such displacement, a contact area between the spacer and the array substrate may change. At the moment when the external force is cancelled, it is difficult for the deformed spacer to return to its initial state due to the change of the contact area. Hence, at some regions where the spacers are displaced relative to the array substrate to a great extent, light may not be shielded by black matrices on the color filter substrate, and light leakage may occur, resulting in uneven brightness of the display panel. Such a phenomenon may be called as "mura". The severity of the mura is in direct proportion to the relative displacement of the spacer. The larger the displacement, the region where the light leakage occurs, the larger the brightness at this region, and the higher the mura level.

Currently, the mura level is generally determined through human eyes. To be specific, display panel samples with mura may be selected through human eyes, and the corresponding mura levels may be determined. Then, a to-be-tested display panel may be tested by a tester, so as to subjectively determine the mura level of the to-be-tested display panel by comparing it with the samples. However, there are the following drawbacks. Because the mura level is tested by the tester's eyes, it is difficult to ensure the accuracy of a test result. In addition, due to the limitation of human eyes, it is impossible for the tester to record the mura at different regions accurately at any time, so the accuracy of the test result may also be adversely affected.

SUMMARY

The present disclosure provides a method and a device for measuring a mura level of a liquid crystal display device, so as to measure the mura level in an accurate manner.

In one aspect, the present disclosure provides in some embodiments a method for measuring a mura level of a liquid crystal display device, including steps of: acquiring correspondence between standard brightness data differences and standard mura levels; acquiring first initial brightness data of a to-be-tested liquid crystal display device when the to-be-tested liquid crystal display device displays a test image; applying a predetermined external force to the to-be-tested liquid crystal display device, and acquiring first effective brightness data of the to-be-tested liquid crystal display device; and acquiring a measurement brightness data difference between the first initial brightness data and the first effective brightness data, and acquiring a mura level corresponding to the measurement brightness data difference in accordance with the correspondence.

In another aspect, the present disclosure provides in some embodiments a device for measuring a mura level of a liquid crystal display device, including: a first acquisition unit configured to acquire correspondence between standard brightness data differences and standard mura levels; a second acquisition unit configured to acquire first initial brightness data of a to-be-tested liquid crystal display device when the to-be-tested liquid crystal display device displays a test image; a third acquisition unit configured to apply a predetermined external force to the to-be-tested liquid crystal display device, and acquire first effective brightness data of the to-be-tested liquid crystal display device; and a determination unit configured to acquire a measurement brightness data difference between the first initial brightness data and the first effective brightness data, and acquire a mura level corresponding to the measurement brightness data difference in accordance with the correspondence.

According to the embodiments of the present disclosure, the correspondence between the standard brightness data differences and the standard mura levels is acquired at first, and then the measurement brightness data difference of the to-be-tested liquid crystal display device before and after the measurement is acquired. As a result, it is able to acquire the mura level corresponding to the measurement brightness data difference in an accurate manner in accordance with the correspondence.

DESCRIPTION OF THE DRAWINGS

In order to illustrate the technical solutions of the present disclosure or the related art in a clearer manner, the drawings desired for the present disclosure or the related art will be described hereinafter briefly. Obviously, the following drawings merely relate to some embodiments of the present disclosure, and based on these drawings, a person skilled in the art may obtain the other drawings without any creative effort.

DETAILED DESCRIPTION

As required, detailed embodiments are disclosed herein. However, it is to be understood that the disclosed embodiments are merely exemplary and that various and alternative forms may be employed. The figures are not necessarily to scale. Some features may be exaggerated or minimized to show details of particular components. Therefore, specific structural and functional details disclosed herein are not to be interpreted as limiting, but merely as a representative basis for teaching one skilled in the art.

The mura measurement for a liquid crystal display device is used to measure a compression strength as well as cell thickness uniformity of a display panel, and a mura level is a very important index for the quality of the liquid crystal display device. The mura may occur in the case that an external force is applied to the liquid crystal display device which is displaying an image, and the mura level of the liquid crystal display device may be measured in accordance with the severity of the mura. The severity of the mura is in direct proportion to the displacement of a spacer in the display panel under the effect of the external force. In addition, the larger the displacement of the spacer, the larger the area of a region where the light leakage occurs, the higher the brightness at the region, and the severer the resultant mura. Hence, it is able to determine the mura level in accordance with the change of the brightness during the measurement.

The present disclosure will be described hereinafter in conjunction with the drawings and embodiments. The following embodiments are for illustrative purposes only, but shall not be used to limit the scope of the present disclosure.

Figure 1:
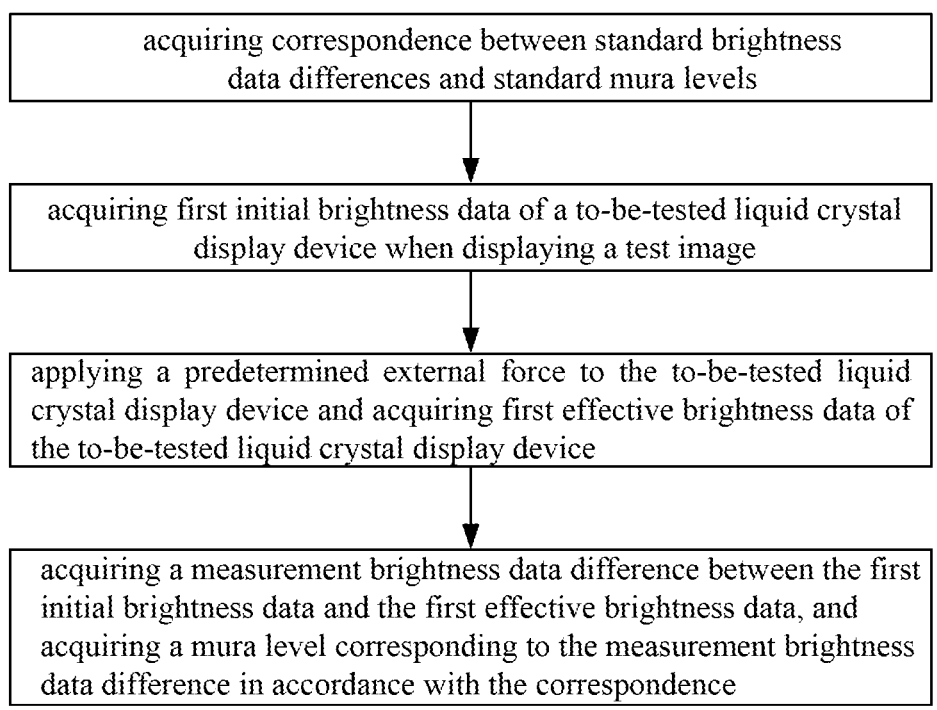
FIG. 1 is a flow chart of a method for measuring a mura level of a liquid crystal display device according to one embodiment of the present disclosure.

The present disclosure provides in some embodiments a method for measuring a mura level of a liquid crystal display device, so as to determine the mura level of a to-be-tested liquid crystal display device in an accurate manner. As shown in FIG. 1, the method includes steps of: acquiring a correspondence between a standard brightness data difference $\Delta A_n$ and a standard mura level $L_n$, where n is a positive integer; acquiring first initial brightness data $A_0$ of the to-be-tested liquid crystal display device when a test image is displayed by the to-be-tested liquid crystal display device; applying a predetermined external force to the to-be-tested liquid crystal display device, and acquiring first effective brightness data $A_1$ of the to-be-tested liquid crystal display device; and acquiring a measurement brightness data difference $\Delta A$ between the first initial brightness data $A_0$ and the first effective brightness data $A_1$, and acquiring a mura level corresponding to the measurement brightness data difference $\Delta A$ in accordance with the correspondence.

According to the method in the embodiments of the present disclosure, it is able to accurately acquire the mura level of the to-be-tested liquid crystal display device through quantitative data analysis, thereby to prevent the occurrence of an artificial error due to the measurement through human eyes.

The test image may be a 64-grayscale or 127-grayscale image. The grayscale image is of an identical color, and the brightness thereof may not be adversely affected by different colors, so it is able to reflect the change of brightness data of the liquid crystal display device in a better manner.

In some embodiments of the present disclosure, when the test image is displayed by the to-be-tested liquid crystal display device, the predetermined external force may be applied to the to-be-tested liquid crystal display device, so as to generate the mura and measure the mura level. In order to increase the measurement accuracy, the predetermined external force may be applied continuously at a certain frequency and a certain speed within a certain time period. In this way, it is able to acquire the first effective brightness data $A_1$ of the to-be-tested liquid crystal display device in a better manner. For example, an external force of 2N may be applied to the to-be-tested liquid crystal display device five times at a speed of 40 mm/s within 5 s. Optionally, the predetermined external force may be applied to an identical test region of the to-be-tested liquid crystal display device.

To be specific, before and after the measurement, in the case that a difference between the measurement brightness data difference $\Delta A$ of the to-be-tested liquid crystal display device (i.e., a difference between the first initial brightness data $A_0$ and the first effective brightness data $A_1$) and the standard brightness data difference $\Delta A_n$ is smaller than a predetermined value, the mura level of the to-be-tested liquid crystal display device may be determined as the standard mura level $L_n$ corresponding to the standard brightness data difference $\Delta A_n$.

In the embodiments of the present disclosure, the liquid crystal display device may be provided with six standard mura levels, i.e., $L_0$, $L_1$, $L_2$, $L_3$, $L_4$ and $L_5$, and the corresponding standard brightness data differences are $\Delta A_0$, $\Delta A_1$, $\Delta A_2$, $\Delta A_3$, $\Delta A_4$ and $\Delta A_5$. There are the following correspondences between the standard brightness data differences and the standard mura levels: A $A_0$-$L_0$, $\Delta A_1$-$L_1$, $\Delta A_2$-$L_2$, $\Delta A_3$-$L_3$, $\Delta A_4$-$L_4$ and $\Delta A_5$-$L_5$.

The standard brightness data difference $\Delta A_n$ is a brightness difference of a standard liquid crystal display device before and after the measurement, the standard liquid crystal display device is provided with the standard mura level $L_n$, so it is able to acquire the correspondence between the standard brightness data difference $\Delta A_n$ and the standard mura level $L_n$. The mura level of the standard liquid crystal display device may be measured under a condition identical to the to-be-tested liquid crystal display device, so as to accurately measure the mura level of the to-be-tested liquid crystal display device in accordance with the correspondence between the standard brightness data difference $\Delta A_n$ and the standard mura level $L_n$. The measurement condition includes an image to be displayed, and a magnitude and an application mode of the force. The step of acquiring the correspondence between the standard brightness data difference $\Delta A_n$ and the standard mura level $L_n$ may include: acquiring the standard mura level $L_n$ of the standard liquid crystal display device when the test image is displayed by the standard liquid crystal display device; acquiring second initial brightness data $A_0'$ of the standard liquid crystal display device when the test image is displayed by the standard liquid crystal display device; applying the predetermined external force to the standard liquid crystal display device to enable the mura level of the standard liquid crystal display device to be the standard mura level $L_n$, and acquiring second effective brightness data $A_1'$ of the standard liquid crystal display device; acquiring the standard brightness data difference $\Delta A_n$ between the second initial brightness data $A_0'$ and the second effective brightness data $A_1'$; and storing the correspondence between the standard brightness data difference $\Delta A_n$ and the standard mura level $L_n$.

In the above steps, the mura level of the standard liquid crystal display device may be measured under a condition identical to the to-be-tested liquid crystal display device, so that a difference between the measurement brightness data difference ΔA of the to-be-tested liquid crystal display device before and after the measurement and the standard brightness data difference $\Delta A_n$ of the standard liquid crystal display device before and after the measurement is smaller than a predetermined value. In this way, it is able to accurately determine the mura level of the to-be-tested liquid crystal display device as the standard mura level $L_n$ of the standard liquid crystal display device.

In the case of acquiring the standard brightness data difference $\Delta A_n$ of the standard liquid crystal display device, the predetermined external force may be applied to the standard liquid crystal display device, so as to generate the mura with the standard mura level. In order to increase the measurement accuracy, the predetermined external force may be applied continuously to the standard liquid crystal display device at a certain frequency and a certain speed within a certain time period. In this way, it is able to acquire the second effective brightness data $A_1'$ of the standard liquid crystal display device in a better manner. For example, an external force of 2N may be applied to the standard liquid crystal display device five times at a speed of 40 mm/s within 5 s. Optionally, the predetermined external force may be applied to an identical test region of the standard liquid crystal display device.

Further, the step of acquiring the standard mura level $L_n$ of the standard liquid crystal display device in the case that the test image is displayed may include: storing correspondences between a plurality of standard images and corresponding mura levels, each standard image being a test image provided with a corresponding mura level; and after applying the predetermined external force, comparing the test image displayed by the standard liquid crystal display device with the plurality of standard images, and in the case that the displayed test image is identical to one of the standard images, determining the standard mura level $L_n$ of the standard liquid crystal display device as a mura level of the one of the standard images.

Through the above steps, it is able to accurately acquire the standard mura level $L_n$ of the standard liquid crystal display device in the case that the test image is displayed.

In the above-mentioned method, the standard mura level $L_n$ of the standard liquid crystal display device may be acquired in advance, and then the standard brightness data difference $\Delta A_n$ of the standard liquid crystal display device before and after the measurement may be acquired. In this way, it is able to acquire the correspondence between the standard brightness data difference $\Delta A_n$ and the standard mura level $L_n$.

Of course, the standard mura level $L_n$ may also be determined merely in accordance with the standard brightness data difference $\Delta A_n$ (i.e., $A1'-A0'$) of the standard liquid crystal display device before and after the measurement. To be specific, in the case that $\Delta A0/A0'$ is less than or equal to 0.04, it means that no light leakage, i.e., no mura, occurs, and at this time, the standard mura level of the standard liquid crystal display device is $L_0$. In the case that $\Delta A_1/A_0'$ is greater than 0.04 and less than or equal to 0.08, the standard mura level of the standard liquid crystal display device is $L_1$. In the case that $\Delta A_2/A_0'$ is greater than 0.08 and less than or equal to 0.1, the standard mura level of the standard liquid crystal display device is $L_2$. In the case that $\Delta A_3/A_0'$ is greater than 0.1 and less than or equal to 0.14, the standard mura level of the standard liquid crystal display device is $L_3$. In the case that $\Delta A_4/A_0'$ is greater than 0.14 and less than or equal to 0.16, the standard mura level of the standard liquid crystal display device is $L_4$. In the case that $\Delta A_5/A_0'$ is greater than 0.16 and less than or equal to 0.2, the standard mura level of the standard liquid crystal display device is $L_5$.

Then, the step of acquiring the correspondence between the standard brightness data difference $\Delta A_n$ and the standard mura level $L_n$ may include: acquiring second initial brightness data $A_0'$ of the standard liquid crystal display device in the case that the test image is displayed; applying the predetermined external force to the standard liquid crystal display device, and acquiring second effective brightness data $A_1'$ of the standard liquid crystal display device; acquiring the standard brightness data difference $\Delta A_n$ between the second initial brightness data $A_0'$ and the second effective brightness data $A_1'$, and determining the standard mura level $L_n$ corresponding to the standard brightness data difference $\Delta A_n$; and storing the correspondence between the standard brightness data difference $\Delta A_n$ and the standard mura level $L_n$.

Figure 4:
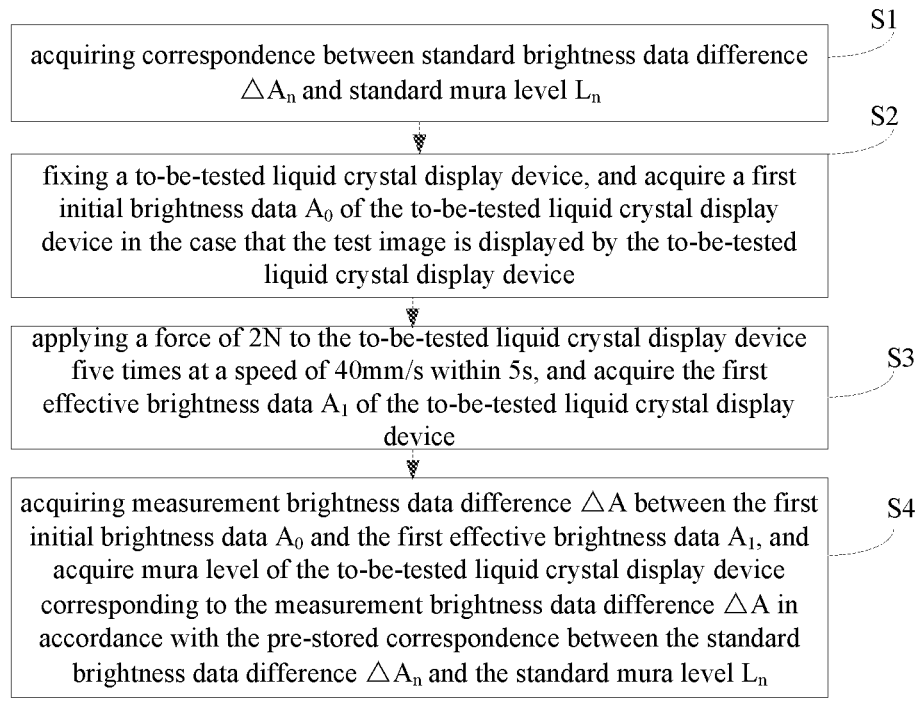
FIG. 4 is a flow chart of a method for measuring a mura level of a liquid crystal display device according to one embodiment of the present disclosure.

In some embodiments of the present disclosure, the measurement method may include the following steps S1-S4, as shown in FIG. 4.

Figure 5:
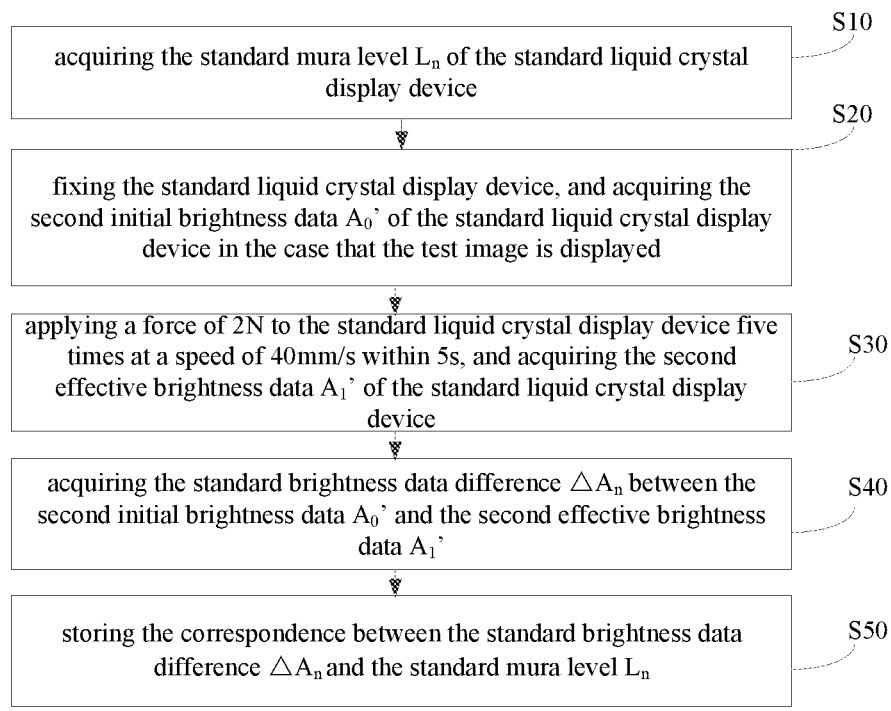
FIG. 5 is a flow chart of the step of acquiring correspondence between a standard brightness data difference and a standard mura level shown in FIG. 4.

Step S1 is to acquire the correspondence between the standard brightness data difference $\Delta A_n$ and the standard mura level $L_n$. To be specific, as shown in FIG. 5, Step S1 includes: Step S10 of acquiring the standard mura level $L_n$ of the standard liquid crystal display device; Step S20 of fixing the standard liquid crystal display device, and acquiring the second initial brightness data $A_0'$ of the standard liquid crystal display device in the case that the test image is displayed; Step S30 of applying a force of 2N to the standard liquid crystal display device five times at a speed of 40 mm/s within 5 s, and acquiring the second effective brightness data $A_1'$ of the standard liquid crystal display device; Step S40 of acquiring the standard brightness data difference $\Delta A_n$ between the second initial brightness data $A_0'$ and the second effective brightness data $A_1'$; and Step S50 of storing the correspondence between the standard brightness data difference $\Delta A_n$ and the standard mura level $L_n$.

Figure 6:
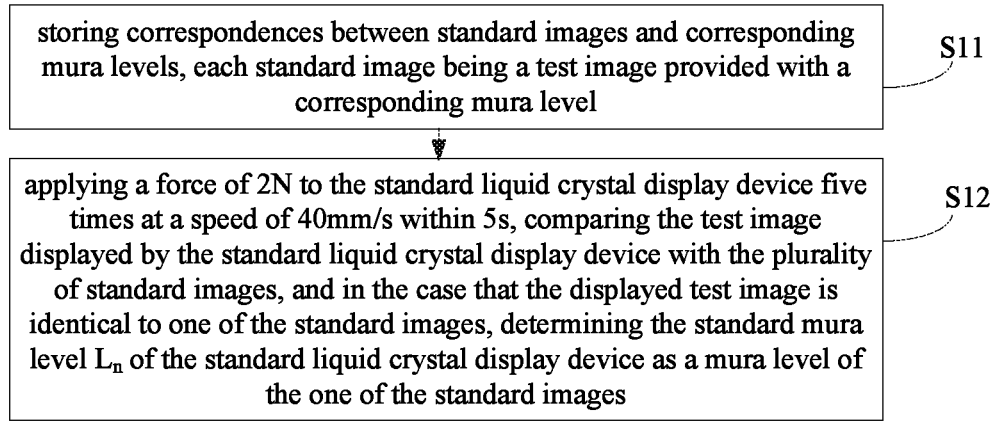
FIG. 6 is a flow chart of the step of acquiring the standard mura level of the standard liquid crystal display device shown in FIG. 5.

To be specific, as shown in FIG. 6, Step S10 includes: Step S11 of storing correspondences between the plurality of standard images and corresponding mura levels, each standard image being a test image provided with a corresponding mura level; and Step S12 of applying a force of 2N to the standard liquid crystal display device five times at a speed of 40 mm/s within 5 s, comparing the test image displayed by the standard liquid crystal display device with the plurality of standard images, and in the case that the displayed test image is identical to one of the standard images, determining the standard mura level $L_n$ of the standard liquid crystal display device as a mura level of the one of the standard images.

Step S2 is to fix the to-be-tested liquid crystal display device, and acquire the first initial brightness data $A_0$ of the to-be-tested liquid crystal display device in the case that the test image is displayed by the to-be-tested liquid crystal display device.

Step S3 is to apply a force of 2N to the to-be-tested liquid crystal display device five times at a speed of 40 mm/s within 5 s, and acquire the first effective brightness data $A_1$ of the to-be-tested liquid crystal display device.

Step S4 is to acquire the measurement brightness data difference ΔA between the first initial brightness data $A_0$ and the first effective brightness data $A_1$, and acquire the mura level of the to-be-tested liquid crystal display device corresponding to the measurement brightness data difference ΔA in accordance with the pre-stored correspondence between the standard brightness data difference $\Delta A_n$ and the standard mura level $L_n$.

Figure 2:
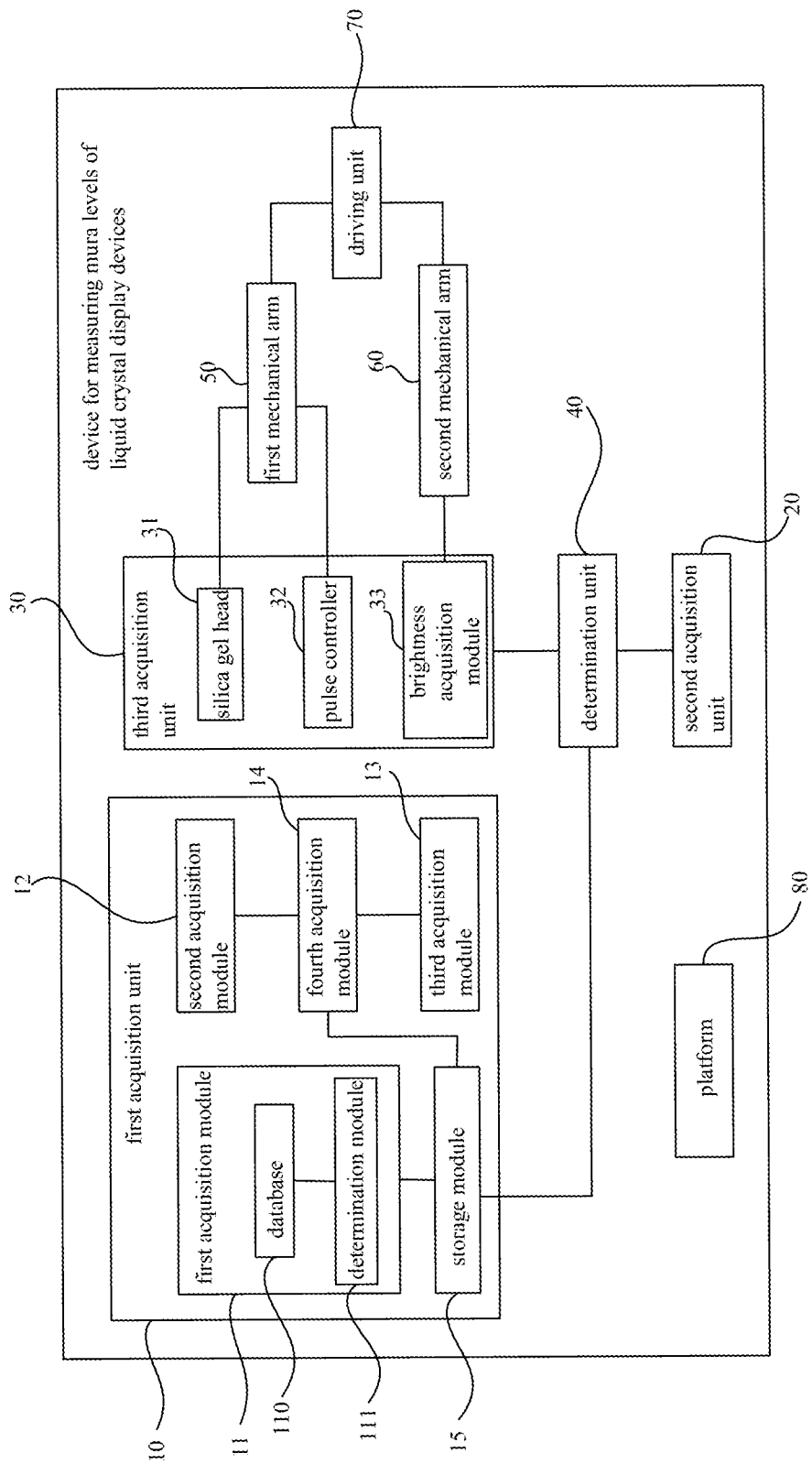
FIG. 2 is a block diagram of a device for measuring a mura level of a liquid crystal display device according to one embodiment of the present disclosure.

Based on an identical inventive concept, the present disclosure provides in some embodiments a device for measuring a mura level of a liquid crystal display device. As shown in FIG. 2, the device includes a first acquisition unit 10, a second acquisition unit 20, a third acquisition unit 30 and a determination unit 40. The first acquisition unit 10 is to acquire a correspondence between the standard brightness data difference $\Delta A_n$ and the standard mura level $L_n$. The second acquisition unit 20 is to acquire the first initial brightness data $A_0$ of the to-be-tested liquid crystal display device in the case that the test image is displayed. The third acquisition unit 30 is to apply the predetermined external force to the to-be-tested liquid crystal display device, and acquire the first effective brightness data $A_1$ of the to-be-tested liquid crystal display device. The determination unit 40 is to acquire the measurement brightness data difference ΔA between the first initial brightness data $A_0$ and the first effective brightness data $A_1$ and acquire a mura level corresponding to the measurement brightness data difference ΔA in accordance with the correspondence.

According to the measurement device in the embodiments of the present disclosure, it is able to quickly and accurately acquire the mura level of the to-be-tested liquid crystal display device through quantitative data analysis.

The standard brightness data difference $\Delta A_n$ is a brightness difference of a standard liquid crystal display device before and after the measurement, the standard liquid crystal display device is provided with the standard mura level $L_n$, so it is able to acquire the correspondence between the standard brightness data difference $\Delta A_n$ and the standard mura level $L_n$. The mura level of the standard liquid crystal display device may be measured under a condition identical to the to-be-tested liquid crystal display device, so as to accurately measure the mura level of the to-be-tested liquid crystal display device in accordance with the correspondence between the standard brightness data difference $\Delta A_n$ and the standard mura level $L_n$. The measurement condition includes an image to be displayed, and a magnitude and an application mode of the force.

The first acquisition unit 10 includes a first acquisition module 11, a second acquisition module 12, a third acquisition module 13, a fourth acquisition module 14 and a storage module 15. The first acquisition module 11 is to acquire the standard mura level $L_n$ of the standard liquid crystal display device in the case that the test image is displayed. The second acquisition module 12 is to acquire the second initial brightness data $A_0'$ of the standard liquid crystal display device in the case that the test image is displayed. The third acquisition module 13 is to apply the predetermined external force to the standard liquid crystal display device so as to enable the mura level of the standard liquid crystal display device to be the standard mura level $L_n$, and acquire the second effective brightness data $A_1'$ of the standard liquid crystal display device in the case that the test image is displayed. The fourth acquisition module 14 is to acquire the standard brightness data difference $\Delta A_n$ between the second initial brightness data $A_0'$ and the second effective brightness data $A_1'$. The storage module 15 is to store the correspondence between the standard brightness data difference $\Delta A_n$ and the standard mura level $L_n$.

The mura level of the standard liquid crystal display device may be acquired by the first acquisition unit 10 under a condition identical to the to-be-tested liquid crystal display device, so that a difference between the measurement brightness data difference ΔA of the to-be-tested liquid crystal display device before and after the measurement and the standard brightness data difference $\Delta A_n$ of the standard liquid crystal display device before and after the measurement is smaller than a predetermined value. In this way, it is able to accurately determine the mura level of the to-be-tested liquid crystal display device as the standard mura level $L_n$ of the standard liquid crystal display device.

Further, the first acquisition module 11 includes a database 110 and a determination module 111. The database 110 is to store the correspondences between the plurality of standard images and the corresponding mura levels, and each standard image is a test image provided with a corresponding mura level. The determination module 111 is to, after the application of the predetermined external force, compare the test image displayed by the standard liquid crystal display device with the plurality of standard images, and in the case that the displayed test image is identical to one of the standard images, determine the standard mura level $L_n$ of the standard liquid crystal display device as a mura level of the one of the standard images.

According to the above-mentioned measurement device, the standard mura level $L_n$ of the standard liquid crystal display device may be acquired in advance, and then the standard brightness data difference $\Delta A_n$ of the standard liquid crystal display device before and after the measurement may be acquired. In this way, it is able to acquire the correspondence between the standard brightness data difference $\Delta A_n$ and the standard mura level $L_n$.

Of course, the standard mura level $L_n$ may also be determined merely in accordance with the standard brightness data difference $\Delta A_n$ (i.e., $A1'-A0'$) of the standard liquid crystal display device before and after the measurement. To be specific, the first acquisition unit 10 includes the second acquisition module 12, the third acquisition module 13, the fourth acquisition module 14 and the storage module 15. The second acquisition module 12 is to acquire the second initial brightness data $A_0'$ of the standard liquid crystal display device in the case that the test image is displayed. The third acquisition module 13 is to apply the predetermined external force to the standard liquid crystal display device, and acquire the second effective brightness data $A_1'$ of the standard liquid crystal display device. The fourth acquisition module 14 is to acquire the standard brightness data difference $\Delta A_n$ between the second initial brightness data $A_0'$ and the second effective brightness data $A_1'$, and determine the standard mura level $L_n$ corresponding to the standard brightness data difference $\Delta A_n$. The storage module 15 is to store therein the correspondence between standard brightness data difference $\Delta A_n$ and the standard mura level $L_n$.

During the measurement of the mura level, an application mode of the external force is very critical, and it may determine the accuracy of the acquired effective brightness data. In some embodiments of the present disclosure, a silica gel head 31 may be used to apply the external force to the liquid crystal display device, so as to prevent the liquid crystal display device from being damaged. A force-application surface of the silica gel head 31 in contact with the liquid crystal display device may have a shape and an area corresponding to the test region. The force-application surface may have, but not limited to, a square shape with a side having a length of 5 mm, 8 mm or 10 mm.

In the embodiments of the present disclosure, the third acquisition unit 30 is to apply the predetermined external force to the to-be-tested liquid crystal display device, so as to acquire the first effective brightness data $A_1$ of the to-be-tested liquid crystal display device in the case that the test image is displayed. The third acquisition unit 30 includes the silica gel head 31, a pulse controller 32 and a brightness acquisition module 33. The silica gel head 31 is to apply the predetermined external force to the to-be-tested liquid crystal display device. The pulse controller 32 is to control the application of the predetermined external force by the silica gel head at a certain frequency and a certain speed within a certain time period. The brightness acquisition module 33 is to acquire the first effective brightness data $A_1$ of the to-be-tested liquid crystal display device during the measurement. The third acquisition unit 30 is further to apply the predetermined external force to the standard liquid crystal display device, and acquire the second effective brightness data $A_1'$ of the standard liquid crystal display device during the measurement. Further, the second acquisition unit 20 may be to not only acquire the first initial brightness data $A_0$ of the to-be-tested liquid crystal display device but also acquire the second initial brightness data $A_0'$ of the standard liquid crystal display device in the case that the test image is displayed. The brightness acquisition module 33 and the second acquisition unit 20 may be an identical high-precision luminometer (e.g., a CA-310 optical probe).

In addition, when acquiring the brightness data of the liquid crystal display device, a platform 80 for carrying the liquid crystal display device may be provided. The platform 80 has a flat surface, so as to carry the liquid crystal display device horizontally. The platform 80 is also to fix thereon the liquid crystal display device, so as to apply the predetermined external force to an identical test region of the liquid crystal display device all the time. To be specific, the liquid crystal display device may be fixed through a clamp or by vacuum adsorption.

In order to control the measurement device automatically, the measurement device may further include: a first mechanical arm 50, a second mechanical arm 60, and a driving unit 70. The silica gel head 31 and the pulse controller 32 are arranged on the first mechanical arm 50. The brightness acquisition module 33 is arranged on the second mechanical arm 60. The driving unit 70 is to drive each of the first mechanical arm 50 and the second mechanical arm 60 to a position above the liquid crystal display device.

Figure 3:
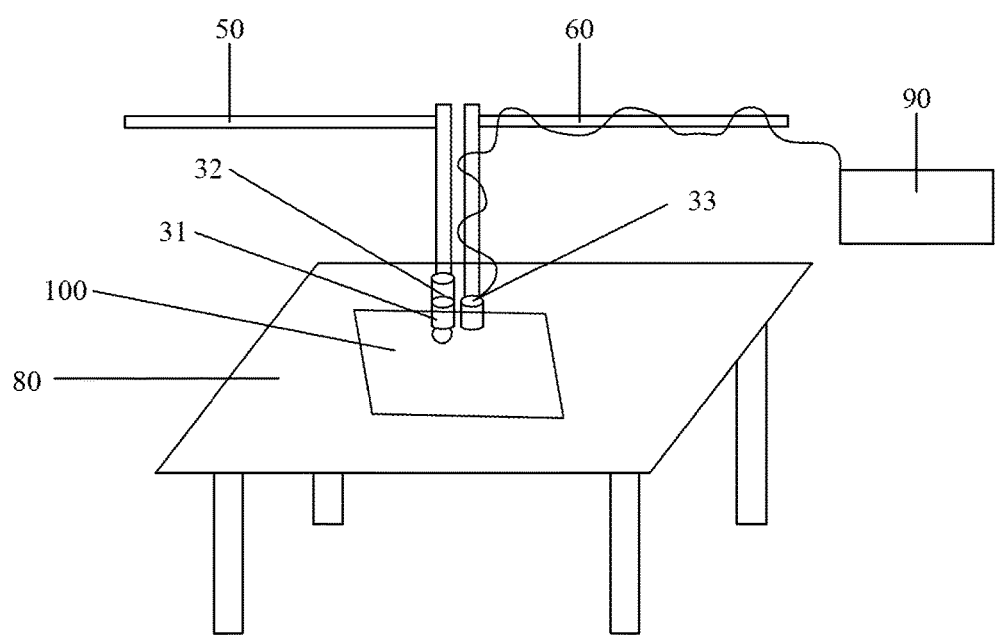
FIG. 3 is a schematic view showing the device for measuring a mura level of a liquid crystal display device according to one embodiment of the present disclosure.

As shown in FIG. 2 in conjunction with FIG. 3, the measurement device includes: the first acquisition unit 10, the second acquisition unit 20, the third acquisition unit 30 and the determination unit 40. The first acquisition unit 10 is to acquire a correspondence between the standard brightness data difference $\Delta A_n$ and the standard mura level $L_n$. The second acquisition unit 20 is to acquire the first initial brightness data $A_0$ of the to-be-tested liquid crystal display device in the case that the test image is displayed. The third acquisition unit 30 is to apply the predetermined external force to the to-be-tested liquid crystal display device and acquire the first effective brightness data $A_1$ of the to-be-tested liquid crystal display device. The determination unit 40 is to acquire the measurement brightness data difference $\Delta A$ between the first initial brightness data $A_0$ and the first effective brightness data $A_1$, and acquire a mura level corresponding to the measurement brightness data difference $\Delta A$ in accordance with the correspondence.

The first acquisition unit 10 includes the first acquisition module 11, the second acquisition module 12, the third acquisition module 13, the fourth acquisition module 14 and the storage module 15. The first acquisition module 11 is to acquire the standard mura level $L_n$ of the standard liquid crystal display device in the case that the test image is displayed. The second acquisition module 12 is to acquire the second initial brightness data $A_0'$ of the standard liquid crystal display device in the case that the test image is displayed. The third acquisition module 13 is to apply the predetermined external force to the standard liquid crystal display device so as to enable the mura level of the standard liquid crystal display device to be the standard mura level $L_n$, and acquire the second effective brightness data $A_1'$ of the standard liquid crystal display device in the case that the test image is displayed. The fourth acquisition module 14 is to acquire the standard brightness data difference $\Delta A_n$ between the second initial brightness data $A_0'$ and the second effective brightness data $A_1'$. The storage module 15 is to store the correspondence between the standard brightness data difference $\Delta A_n$ and the standard mura level $L_n$.

The first acquisition module 11 includes: the database 110 configured to store the correspondences between the plurality of standard images and the corresponding mura levels, and the determination module 111 configured to, after the application of the predetermined external force, compare the test image displayed by the standard liquid crystal display device with the plurality of standard images, and in the case that the displayed test image is identical to one of the standard images, determine the standard mura level $L_n$ of the standard liquid crystal display device as a mura level of the one of the standard images.

The third acquisition unit 30 includes the silica gel head 31, the pulse controller 32, and the brightness acquisition module 33. The silica gel head 31 is to apply the predetermined external force to the to-be-tested liquid crystal display device. The pulse controller 32 is to control the application of the predetermined external force by the silica gel head at a certain frequency and a certain speed within a certain time period. The brightness acquisition module 33 is to acquire the first effective brightness data $A_1$ of the to-be-tested liquid crystal display device during the measurement. The brightness acquisition module 33 may be an identical to the second acquisition module 20.

The measurement device may further include: the first mechanical arm 50, the second mechanical arm 60, the driving unit 70, the platform 80 and a data collection unit 90. The silica gel head 31 and the pulse controller 32 are arranged on the first mechanical arm 50. The brightness acquisition module 33 is arranged on the second mechanical arm 60. The driving unit 70 is to drive each of the first mechanical arm 50 and the second mechanical arm 60 to a position above the liquid crystal display device. The platform 80 is to support the liquid crystal display device. The data collection unit 90 is connected to the brightness acquisition module 33 and is to collect the first initial brightness data $A_0$ and the first effective brightness data $A_1$ of the to-be-tested liquid crystal display device acquired by the brightness acquisition module 33.

Figure 7:
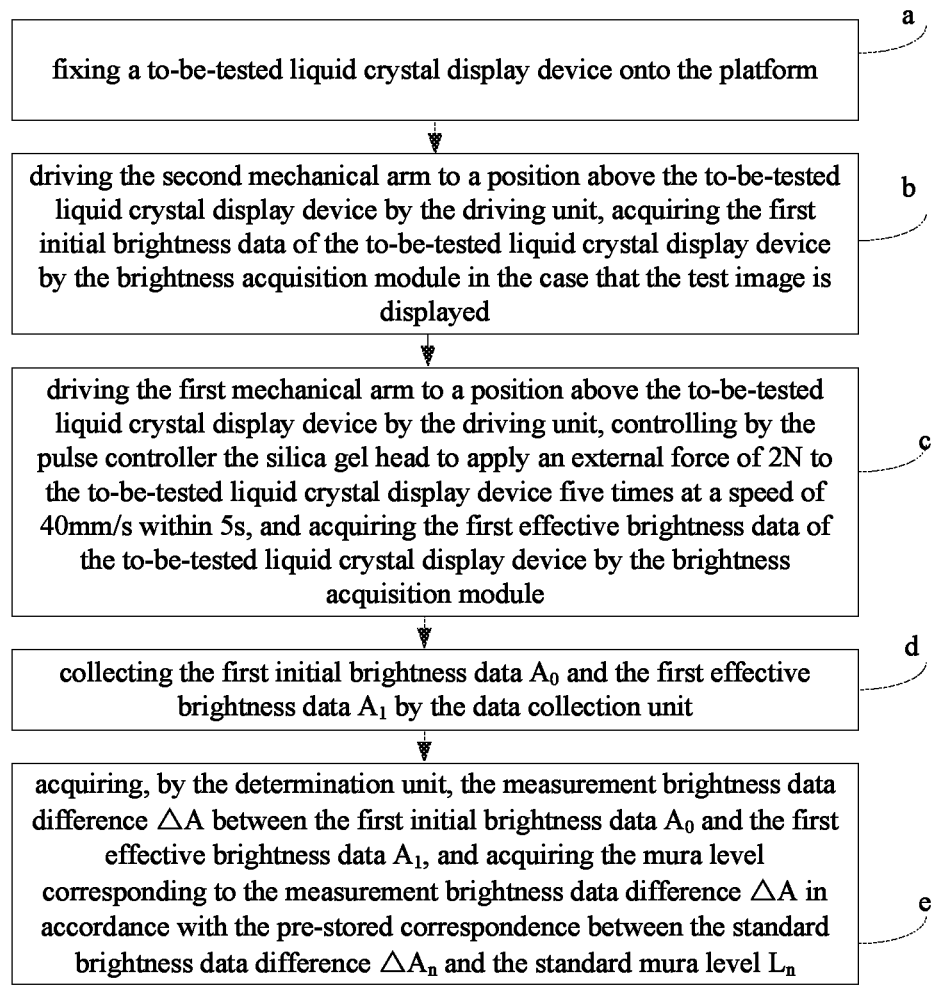
FIG. 7 is a flow chart of a method for measuring a mura level of a liquid crystal display device by using the device for measuring the mura level of the liquid crystal display device shown in FIG. 7.

As shown in FIG. 2 in conjunction with FIG. 3, as well as FIG. 7, the measurement method using the measurement device may include: Step a of fixing the to-be-tested liquid crystal display device 100 onto the platform 80; Step b of driving the second mechanical arm 60 to a position above the to-be-tested liquid crystal display device 100 by the driving unit 70, and acquiring the first initial brightness data of the to-be-tested liquid crystal display device 100 by the brightness acquisition module 33 in the case that the test image is displayed; Step c of driving the first mechanical arm 50 to a position above the to-be-tested liquid crystal display device 100 by the driving unit 70, controlling by the pulse controller 32 the silica gel head 31 to apply an external force of 2N to the to-be-tested liquid crystal display device 100 five times at a speed of 40 mm/s within 5 s, and acquiring the first effective brightness data $A_1$ of the to-be-tested liquid crystal display device 100 by the brightness acquisition module 33; Step d of collecting the first initial brightness data $A_0$ and the first effective brightness data $A_1$ by the data collection unit 90; and Step e of acquiring, by the determination unit 40, the measurement brightness data difference $\Delta A$ between the first initial brightness data $A_0$ and the first effective brightness data $A_1$, and acquiring the mura level corresponding to the measurement brightness data difference $\Delta A$ in accordance with the pre-stored correspondence between the standard brightness data difference $\Delta A_n$ and the standard mura level $L_n$.

The above are merely the preferred embodiments of the present disclosure. Obviously, a person skilled in the art may make further modifications and improvements without departing from the spirit of the present disclosure, and these modifications and improvements shall also fall within the scope of the present disclosure.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

What is claimed is:

1. A method for measuring a mura level of a liquid crystal display device, comprising steps of:
    acquiring correspondence between standard brightness data differences and standard mura levels;
    acquiring first initial brightness data of a to-be-tested liquid crystal display device when the to-be-tested liquid crystal display device displays a test image;
    applying a predetermined external force to the to-be-tested liquid crystal display device with a silica gel head, and acquiring first effective brightness data of the to-be-tested liquid crystal display device; and
    acquiring a measurement brightness data difference between the first initial brightness data and the first effective brightness data, and acquiring a mura level corresponding to the measurement brightness data difference in accordance with the correspondence;
    wherein the step of applying the predetermined external force to the to-be-tested liquid crystal display device with the silica gel head, and acquiring the first effective brightness data of the to-be-tested liquid crystal display device comprises:
        applying the predetermined external force to the to-be-tested liquid crystal display device with the silica gel head at a certain frequency and a certain speed within a certain time period.

2. The method according to claim 1, wherein the step of acquiring the correspondence between the standard brightness data differences and the standard mura levels comprises:
    acquiring a standard mura level of a standard liquid crystal display device when the standard liquid crystal display device displays the test image;
    acquiring second initial brightness data of the standard liquid crystal display device when the standard liquid crystal display device displays the test image;
    applying the predetermined external force to the standard liquid crystal display device until a mura level of the standard liquid crystal display device is one of the standard mura levels, and acquiring second effective brightness data of the standard liquid crystal display device;
    acquiring one standard brightness data difference between the second initial brightness data and the second effective brightness data; and
    storing correspondence between the one standard brightness data difference and the one of the standard mura levels.

3. The method according to claim 2, wherein the step of acquiring the standard mura level of the standard liquid crystal display device when the standard liquid crystal display device displays the test image comprises:
    storing correspondence between a plurality of standard images and corresponding mura levels, each of the standard images being one test image with a corresponding mura level; and
    after applying the predetermined external force, comparing the test image displayed by the standard liquid crystal display device with the plurality of standard images; when the test image displayed by the standard liquid crystal display device is identical to one of the standard images, determining the standard mura level of the standard liquid crystal display device as a mura level of the one of the standard images.

4. The method according to claim 1, wherein the step of applying the predetermined external force to the to-be-tested liquid crystal display device with the silica gel head at a certain frequency and a certain speed within a certain time period comprises: applying a force of 2N to the to-be-tested liquid crystal display device five times at a speed of 40 mm/s within 5 s.

5. The method according to claim 1, wherein the step of applying the predetermined external force to the to-be-tested liquid crystal display device with the silica gel head and acquiring the first effective brightness data of the to-be-tested liquid crystal display device comprises:
    applying the predetermined external force to an identical region of the to-be-tested liquid crystal display device with the silica gel head at the certain frequency and the certain speed within the certain time period.

6. The method according to claim 1, wherein the test image has a grayscale of 64 or 127.

* * * * *